United States Patent [19]

Goldemberg et al.

[11] Patent Number: 4,666,708

[45] Date of Patent: May 19, 1987

[54] DENTAL RINSE

[75] Inventors: Robert L. Goldemberg; Allan J. Lazare; Richard Berger, all of New York, N.Y.

[73] Assignee: Oral Research Laboratories, Inc., New York, N.Y.

[21] Appl. No.: 692,821

[22] Filed: Jan. 23, 1985

Related U.S. Application Data

[63] Continuation-in-part of Ser. No. 574,350, Jan. 27, 1984.

[51] Int. Cl.$^4$ ................................ A61K 7/16
[52] U.S. Cl. ...................................... 424/49
[58] Field of Search ..................... 424/49–58

[56] References Cited

U.S. PATENT DOCUMENTS

| | | | |
|---|---|---|---|
| 428,033 | 5/1890 | Alson | 424/58 |
| 1,105,739 | 8/1914 | Wunsche | 424/53 |
| 1,336,272 | 4/1920 | Billing | 424/145 |
| 1,471,987 | 0/0000 | Vogt | 424/37 |
| 1,627,963 | 5/1927 | Fuller | 424/49 |
| 1,716,035 | 6/1929 | Donchi | 424/49 |
| 1,936,456 | 11/1933 | Larson | 167/68 |
| 2,004,957 | 6/1935 | Messner | 167/82 |
| 2,027,535 | 1/1936 | Jacobson | 167/93 |
| 2,035,267 | 3/1936 | Fleischman | 167/93 |
| 2,054,742 | 9/1936 | Elbel | 167/93 |
| 2,069,157 | 1/1937 | Sahyun | 167/93 |
| 2,124,971 | 7/1938 | Eisenberg et al. | 167/93 |
| 2,154,168 | 4/1939 | Klein et al. | 167/93 |
| 3,164,524 | 1/1965 | Fand | 167/93 |
| 3,427,380 | 2/1969 | Kirkland | 424/54 |
| 3,427,381 | 2/1969 | Kirkland | 424/54 |
| 3,629,468 | 12/1971 | Andersen | 424/44 |
| 3,651,207 | 3/1972 | Lauster et al. | 424/50 |
| 3,729,553 | 4/1973 | Gold et al. | 424/44 |
| 3,772,431 | 11/1973 | Mlkvy et al. | 424/44 |
| 3,864,472 | 2/1975 | Pensak et al. | 424/54 |
| 3,887,701 | 6/1975 | Nachtigal | 424/54 |
| 3,888,976 | 6/1975 | Mlkvy et al. | 424/44 |
| 3,947,570 | 3/1976 | Pensak et al. | 424/54 |
| 4,082,841 | 4/1978 | Pader | 424/50 |
| 4,100,269 | 7/1978 | Pader | 424/49 |
| 4,132,770 | 1/1979 | Barth | 424/49 |
| 4,138,477 | 2/1979 | Gaffar | 424/52 |
| 4,150,151 | 4/1979 | Pader et al. | 424/56 |
| 4,152,418 | 5/1979 | Pader | 424/49 |
| 4,154,815 | 5/1979 | Pader | 424/50 |
| 4,224,307 | 9/1980 | Thiele et al. | 424/49 |
| 4,291,017 | 9/1981 | Beierle et al. | 424/52 |
| 4,339,429 | 7/1982 | Raaf et al. | 424/47 |
| 4,362,639 | 12/1982 | Eoga | 252/99 |
| 4,370,314 | 1/1983 | Gaffar | 424/54 |

FOREIGN PATENT DOCUMENTS

| | | |
|---|---|---|
| 1126160 | 6/1982 | Canada . |
| 1136990 | 12/1982 | Canada . |
| 0085891 | 1/1983 | European Pat. Off. . |
| 975623 | 4/1962 | Fed. Rep. of Germany . |
| 55-66507 | 5/1980 | Japan . |
| 56-59703 | 5/1981 | Japan . |
| 58-49309 | 3/1983 | Japan . |
| 321765 | 11/1968 | Sweden . |
| 399917 | 10/1933 | United Kingdom . |
| 1469398 | 4/1977 | United Kingdom . |
| 2095694 | 10/1982 | United Kingdom . |

OTHER PUBLICATIONS

Chem. Abs. 95 No. 86321b.
Lamster et al., "Efficacy of Listerine Antiseptic Compared to a Vehicle Control and Water Control in Inhibiting the Development of Dental Plaque and Gingivitis" (Fairleigh Dickinson University 1982).
Menaker et al., "The Effects of Listerine Antiseptic on Dental Plaque", Ala. J. Med. Sci. vol. II, No. 1 (1979).
Albertini et al., "A Propose de 60 Observations Randomisees sur le Traitement du Tartre Dentaire Avec une Pate au Benzoate de Sodium", L'Information Dentaire du 10/3/1983.
Fluocaril Toothpaste Box and Information.
Konstantinov, Chem. Abs. 78 No. 62202m (USSR 353721).
Sklyar, Chem. Abs. 94 No. 197571g (USSR 808084).
47 Fed. Reg. 22831–22939 (vol. 47, No. 101, 1982).
44 Fed. Reg. 63274–63290 (1979).
Emling and Yankel, "First Clinical Studies of New Prebrushing Mouthrinses", *Compendium of Continuing Education in Dentistry*, vol. VI, No. 9, pp. 636 et seq. (1985).

*Primary Examiner*—Shep K. Rose

[57] ABSTRACT

This invention relates to improved oral compositions for dental hygiene, and, in particular, to dental rinse formulations which upon application to the teeth, loosen plaque present on dental surfaces and render it more amenable to removal during brushing with a conventional dentifrice.

28 Claims, No Drawings

DENTAL RINSE

This application is a continuation-in-part of a copending application of Goldemberg et al, Ser. No. 574,350, filed Jan. 27, 1984.

FIELD OF THE INVENTION

This invention relates to improved oral compositions for dental hygiene, and, in particular, to dental rinse formulations which upon application to the teeth, loosen plaque present on dental surfaces and render it more amenable to removal during brushing with a conventional dentifrice.

BACKGROUND OF THE INVENTION

Dental plaque is present to some degree, in the form of a film, on virtually all dental surfaces. It is a by-product of microbial growth, and comprises a dense microbial layer consisting of a mass of microorganisms embedded in a polysaccharide matrix. The microorganisms present in plaque are mainly coccoidal organisms, particularly in early plaque, which, in the mouths of some persons at least, change to filamentous organisms after a few days. Plaque itself adheres firmly to dental surfaces and is removed only with difficulty even through a rigorous brushing regimen. Moreover, plaque rapidly reforms on the tooth surface after it is removed.

A wide variety of microorganisms are found in the oral cavity, and among these are gram-positive anaerobic rods associated with the development of plaque such as *Corynebacterium, Nocardia, Neisseria* and *Streptococci*, such as *S. mutens, S. bovis, S. salivarius*, and gram-positive *streptococci* of the genus *Peptostreptooccus* (See Robert J. Fitzgerald in "The Alabama Journal of Medical Sciences" Volume 5, No. 3, July, 1968, pp. 241-242).

In addition to the aforementioned microorganisms, there is also present in plaque relatively small amounts of other substances such as salivary proteins, carbohydrates, epithelial cells and leucocytes. These organisms play a key role in the etiology of plaque. The bacterial organisms associated with plaque formation produce a capsular material which apparently causes the cells of the organism to adhere to each other, holding the plaque together and allowing for further growth. For example, one of the capsule forming bacteria which occurs in large numbers in early plaque is *Neisseria sicca*.

Plaque may form on any part of the tooth surfaces, and is found particularly at the gingival margin, in cracks in the enamel, and on the surface of dental calculus. As discussed in greater detail below, the danger associated with the formation of plaque on the teeth lies in the tendency of plaque to build up and eventually produce gingivitis, periodontitis and other types of periodontal disease, as well as dental caries and dental calculus.

More specifically, dental plaque is a precursor to the formation of the hard crystalline buildup on teeth referred to as dental calculus. Both the bacterial and the nonbacterial components of plaque mineralize to form calculus, whicn comprises mineralized bacteria as well as organic constituents, such as epithelial cells, live bacteria, salivary proteins, leucocytes, and crystals of substances having molecularly bound calcium and phosphorus, e.g., hydroxyapatite, $3[Ca_3(PO_4)_2]Ca(OH)_2$, octacalcium phosphate, $Ca_8(HPO_4)_2(PO_4)_4.5H_2O$, brushite, $CaHPO_4.2H_2O$, and whitlockite, which is considered to have the formula $beta-Ca_3(PO_4)_2$. Dental plaque and, hence, calculus are particularly prone to form at the ginqival margin, i.e., the junction of the tooth and gingiva. The buildup of plaque at the gingival margin is believed to be the prime cause of gingivitis and other periodontal disorders.

Regular tooth brushing with a conventional dentifrice for some persons greatly retards or even prevents the accumulation of significant amounts of plaque and calculus. For other persons, however, plaque builds up rapidly even with regular brushing, which, in turn, leads to the formation of calculus, caries, and presents the danger of periodontal diseases. Removal by a dentist is currently the only safeguard against serious gingival inflammation caused by the accumulation of significant amounts of of plaque in some individuals. It is widely recognized in dentistry that a rigorous brushing regimen alone for many individuals will not prevent the formation of significant amounts of plaque.

Mouthwashes are employed in conventional regimens of oral hygiene. However, conventional mouthwashes serve primarily to sweeten the breath, are formulated for that purpose, and are believed not to function in any significant way to loosen or remove plaque from the dental surfaces. Moreover, since the user typically does not employ a mouthwash expressly for the purpose of cleansing the teeth of plaque, mouthwashes are not routinely used immediately prior to brushing as a way of rendering plaque and/or calculus more amenable to removal during the subsequent brushing process.

There is, therefore, a definite need in the art for an oral hygiene composition which, when used alone, or in conjunction with a regular tooth brushing regimen, renders the plaque present on the dental surface more susceptible to removal during a subsequent brushing regimen employing a conventional dentifrice.

In view of the foregoing, it is an object of this invention to provide an improved dental rinse which has a detersive effect upon plaque, and which functions to loosen the plaque present on dental surfaces, and thereby to aid in the reduction of caries formation, and to deter the development of calculus and oral diseases associated with excessive plaque formation such as gingivitis and periodontitis.

It is also an objective of this invention to provide an improved method of dental hygiene, and for removing, loosening and retarding the further development of plaque on dental surfaces.

BRIEF DESCRIPTION OF THE INVENTION

In accordance with the foregoing objectives, this invention provides a dental rinse intended for application to dental surfaces for the purpose of loosening the adherence of plaque present on the teeth, and retarding the further accumulation of plaque on the treated dental surfaces. The dental rinse of this invention which comprises an alkaline solution with a pH of at least about 7.5 or above, includes detersive amounts of an oral surfactant and a detergent builder for the oral surfactant in a liquid carrier.

In preferred embodiments of this invention the dental rinse comprises an alkaline solution with a pH of at least about 7.5 or above (preferably about 8.0 to 9.0) which includes in a liquid carrier detersive amounts of an oral surfactant, a detergent builder for the oral surfactant, and at least about 1% by weight of sodium benzoate. It has been found that when sodium benzoate is employed in the alkaline dental rinse described above, the ability of the formulation to loosen plaque and to prevent plaque buildup subsequent to the application of the dental rinse is unexpectedly and significantly enhanced. It is also preferred to employ a nonionic oral surfactant in combination with sodium borate as the detergent building component of the dental rinse.

In further embodiments of the dental rinse of this invention, minor effective amounts of colorant, flavorant, antiseptics, healing agents and other additives are advantageously employed in combination with the other ingredients. More specifically, formulations of the dental rinse of this invention may include antiseptically effective amounts of sodium salicylate, ethanol (which may also serve as all or part of the liquid carrier), and an antiseptically active flavorant, e.g., thymol/eucalyptol menthol. Of course, sodium benzoate itself imparts antiseptic properties to the formulation. Formulations, containing the foregoing ingredients, serve to sooth gums irritated from brushing, and when healing agents are employed, to actually enhance the rate of healing of gums and associated tissues which may have become irritated during brushing or due to an existing periodontal disorder such as gingivitis.

This invention also provides a method for loosening plaque from dental surfaces which comprises the step of applying the dental rinse composition described above to the dental surfaces of the oral cavity. In preferred embodiments of the method of this invention, the rinse is applied to the dental surfaces immediately prior to the step of brushing the teeth with a conventional dentifrice. It is believed that the dental rinse of this invention renders the plaque present on dental surfaces quite susceptible to subsequent removal during an ordinary brushing process.

The dental rinse of this invention may be applied to the surface of the teeth by any conventional process. Preferably, however, the dental rinse is applied by placing a comfortable amount of the dental rinse in the oral cavity and then circulating the rinse about the mouth with the intention of thoroughly soaking the teeth and gums.

The dramatic reduction in plaque content accomplished through the use of the dental rinse and associated methods of this invention should also serve both to reduce dental caries closely associated with plaque buildup, as well as preventing or ameliorating plaque and plaque-associated oral disorders such as gingivitis and periodontitis.

Further advantages and objectives of this invention will be apparent from the detailed description of the invention which follows.

DETAILED DESCRIPTION OF THE INVENTION

The dental rinse formulations of this invention comprise an alkaline solution having a pH of at least about 7.5 or above, preferably about 8.0 or above, of detersive amounts of an oral surfactant and a detergent builder therefor in a liquid carrier. The liquid carrier may be water or a solution of water and alcohol (ethanol). The liquid carrier may comprise from about 70% to about 95% of the formulation, e.g., the formulation may include as the liquid carrier a component of about 65% to 95% water and about 5% to 35% ethanol.

The oral surfactants employed in the dental rinse of this invention are those surfactants which are nontoxic and therefore suitable for use in the oral cavity, and which provide a detersive effect when the formulation containing them is applied in about tablespoon quantities to the oral cavity. As explained below, it is preferable to employ a detergent builder in conjunction with the oral surfactant. The nonionic oral surfactants are preferred for use as the oral surfactant component, although suitable anionic and cationic surfactants may also be employed.

Nonionic oral surfactants which may be employed herein include mixtures of laurate esters of sorbitol and sorbitol anhydrides consisting predominantly of the monoester condensed with about 15 to 25 (e.g. 20) moles of ethylene oxide, such as the commonly available nonionic detergent Tween 20 available from I.C.I. Americas, Wilmington, Delaware; as well as the block polymers of polyoxyethylene and polyoxypropylene, such as Pluronic F108 available from BASF-Wyandotte Co., Wyandotte, Mich. In addition, suitable oral surfactants for use herein include alkyl sulfonates and sulfates such as sodium lauryl sulfate or a sulfonated monoglyceride of a fatty acid having about 10 to about 18 carbon atoms, as well as N-methyl-N-palmitoyl tauride, sodium-N-lauroyl sarcosinate, other sarcosinates, sulfosuccinates, or the like. The oral surfactant is preferably employed in the aqueous or ethanolic solvent of the dental rinse at levels ranging from about 0.1% to about 10% by weight of the composition, and most preferably from about 0.5% to about 2% of the composition. However, in general, the amount of nonionic detergent employed is adjusted to provide the desired degree of detersive effect or, if desired, foam in the oral cavity during use.

Alkaline alkyl sulfates, especially where the longest chain of the alklyl portion ranges from 9 to 15 carbon atoms, when added in concentrations from 0.1% to 1.5% are especially desirable. Dental rinses formed with these oral sufactants display a number of desired characteristics. For instance, when sodium lauryl sulfate is added at a concentration from 0.1% to 1.5%, plaque removal on initial use is high, and unremoved plaque exhibits markedly decreased viability and markedly increased susceptibility to removal by simple mechanical methods. The pH drop that usually occurs shortly after using a rinse is effectively delayed, indicating that production of acid by unremoved plaque has been substantially halted. Furthermore, a rinse formulated with sodium lauryl sulfate is effective at a much greater dilution than is a rinse formulated without such an alkaline alkyl sulfate. Without prejudice to the scope of the invention, it is believed that sodium lauryl sulfate acts as a potentiator for other ingredients of the rinse, thereby increasing their ability to loosen plaque, and their ability to penetrate bacterial colonies.

A detergent builder is employed in combination with the oral surfactant component of the dental rinse. The detergent builders employed herein are nontoxic, orally compatible materials which are distinctly basic in aqueous solution, for example, sodium carbonate, sodium borate, mixtures thereof, or alkaline mixtures of sodium carbonate and/or sodium borate with sodium bicarbonate. Preferably, the detergent builder is sodium borate and is present in amounts ranging from about 0.1% to about 1%, and most preferably, 0.2% to about 0.5% by weight of the rinse formulation. It is believed that the use of a detergent builder in conjunction with the surfactant component of this invention in basic solution enhances the ability of the dental rinse to both loosen and dislodge plaque from dental surfaces during rinsing, while at the same time enhancing the ability of the rinse to maintain the loosened plaque or calculus materials in suspension in the rinse, enabling the user to finally discharge them from the mouth. Significantly, the plaque-loosening effect of the rinse renders the plaque remaining on the dental surface far more amenable to removal during a subsequent brushing process.

When the dental rinse is distinctly basic, as will be the case when sodium borate is employed, sodium bicarbonate is advantageously employed in combination with sodium borate, both for its detergent building properties, as well as for its buffering properties in an aqueous solution. In particular, an amount of sodium bicarbonate may be employed in an aqueous ethanolic, or aqueous/ethanolic solvent base containing one or more distinctly basic ingredients (e.g., sodium borate) in order to adjust the dental rinse to the desired basic pH level discussed above. For example, when sodium borate is employed in the amounts stated above, sodium bicarbonate is preferably employed at levels ranging from about 0.1% to about 1.5%, and most preferably about 0.3% to about 1.0% by weight of the rinse formulation.

As mentioned above, the pH of the dental rinse is about 7.5 or above, and may be adjusted to that pH with sodium bicarbonate or another buffer. The upper limit of the alkaline pH of the composition is limited, however, by the possible irritative effects of strongly alkaline solutions in the oral cavity. Thus, the pH is preferably not above 10.0, and most preferably is between about pH 8.0 to about 9.0.

It has been found that unlike the commercial mouthwash formulations which have an acidic pH, the use of the dental rinse of this invention, comprised of an alkaline solution of an oral surfactant and detergent builder, functions during an ordinary rinsing plus brushing regimen, to reduce the amount of plaque present on dental surfaces during the usage period. It has also been found that when sodium benzoate is employed in combination with the other ingredients of the dental rinse of this invention, the plaque loosening and retarding properties of the composition are significatnly enhanced. Thus, in a preferred embodiment of this invention, the dental rinse comprises an alkaline solution having a pH of at least about 7.5, of a liquid solvent carrier selected from the group consisting of water, ethanol or mixtures thereof containing sodium borate, an oral surfactant, and sodium benzoate. The sodium benzoate is preferably employed at a level of a least about 1% by weight, and most preferably at least about 2% by weight of the composition.

Plaque consists of about 80% live bacteria in a polysaccharide matrix. Therefore, it is desirable for a dental rinse to possess significant antibacterial properties in order to eliminate or retard the growth of the bacterial colonies present in plaque. The relatively high levels of sodium benzoate employed in embodiments of this invention impart antiseptic properties to the formulation. Moreover, in order to advantageously enhance the antiseptic properties of the dental rinse formulations (which may or may not include sodium benzoate) auxiliary antiseptics may be included in the formulation. Further, antiseptic properties may also be imparted to the dental rinse by the use of a liquid carrier comprised of ethanol or ethanol/water, and/or auxiliary antiseptics suitable for use in the oral cavity.

A preferred, antibacterial (and analgesic) additive is sodium salicylate. It is believed that sodium salicylate is advantageously employed in the dental rinse formulation of this invention because it also functions to aid in the solubilization and removal of plaque from the dental surface. In addition to, or in place of sodium salicylate, other oral antiseptics which are soluble in the liquid carrier (i.e., water and/or alcohol) and which are compatible with other ingredients of the formulation may be employed, for example, benzethonium chloride, N-alkyl-pyridinium chloride, N-cetyl pyridinium bromide, sodium N-lauroyl sarcosine, N-myristoyl glycine and potassium N-lauroyl sarcosine. The sodium salicylate or other analgesics preferably comprise about 0.1 to 1%, and most preferably, about 0.2 to about 0.5% by weight of the rinse.

In addition to the foregoing ingredients, the dental rinse of this invention may include adjuvant ingredients effective to provide the desirable flavoring and coloring, and to impart the desired mouthfeel to the formulation. In further embodiments of this dental rinse, the flavorant employed is one which possesses antiseptic properties, e.g. a flavorant based upon thymol, eucalyptol and menthol. Thus, the formulation may include as combined antiseptic ingredients sodium benzoate, sodium salicylate and the above-mentioned antiseptic flavorant or an equivalent antiseptic flavorant. The concentration of the flavorant is adjusted to impart the desired taste and/or degree of antibacterial activity to the overall formulation.

In further embodiments of the dental rinse formulation of this invention, effective amounts of one or more analgesics and/or substances which promote wound healing, i.e., healing agents, are employed. To this end, sodium salicylate discussed above is particularly preferred because of its associated antiseptic and plaque solubilizing properties. The healing agent may be suitably employed at levels, of, for example, 0.1 to about 3%. The preferred healing agent for use herein is allantoin (glyoxyl diuride).

In particular, a combination of a soluble hydrocolloid (e.g. xanthan gum), sodium salicylate and allantoin is advantageously employed for its combined wound healing analgesic properties. That combination of ingredients provides both a soothing effect to gums that may be irritated following brushing, and additionally may enhance the rate of gum-healing due to the debriding and healing action of the allantoin. Sodium bicarbonate also promotes debridement and, hence, it is advantageously employed in the formulation of this invention for that purpose, as well as for the other reasons discussed above.

The dental rinse of this invention may also contain ingredients such as glycerine in amounts up to about 20% by weight, or, for example, about 8% to 18% by weight. The glycerine functions as a sweetener, and also imparts body to the composition (along with the alcohol or any gums present) as well as the desired mouthfeel. Equivalent materials may be employed in place of, or in combination with, the glycerine such as sorbitol and/or propylene glycol.

The dental rinse is prepared by mixing the active ingredients together to form a homogeneous solution of the constituent ingredients. The rinse is used in a conventional manner: that is, by applying a comfortable amount in the mouth, say one tablespoon full, and rinsing it about the dental surfaces. As illustrated by the appended examples, a striking reduction in the amount of plaque on tooth surfaces is accomplished over a relatively brief usage period when the dental rinse of this invention is employed in conjunction with an ordinary tooth brushing regimen.

The manner of making and using the present invention will be illustrated further by the following detailed examples.

EXAMPLE 1

The following dental rinse was formulated:

| Weight Percent | Component |
| --- | --- |
| Portion A-1 | |
| 15.50 | glycerine, USP |
| 0.8 | 01% FDC Red 40 |
| 72.82 | water |
| Portion A-2 | |
| 0.03 | xanthan gum |
| 0.20 | allantoin |
| 0.20 | sodium salicylate |
| Portion A-3 | |
| 0.50 | sodium bicarbonate, USP |
| 0.20 | sodium borate, USP |
| 2.00 | sodium benzoate, NF |
| Portion B | |
| 6.60 | ethanol |
| 0.31 | flavor compound (4483T, Carruba Inc.) |
| 0.84 | Polysorbate 20 |
| 100.00% | |

A dry mix of the portion A-2 ingredients was prepared, and then slowly added to a mixture of the portion A-1 ingredients with high-speed propeller agitation. Also under high-speed agitation, the phase A-3 ingredients were individually added in the listed order, followed by the slow addition of a previously prepared mixture of Portion B to the phase A 1-3 mixture. The resultant dental rinse had a pleasing red appearance and an acceptable mouthfeel. The product was uniform in appearance and did not separate even after prolonged standing at room temperature. The pH of the dental rinse was 7.7.

EXAMPLE 2

Four patients were administered the dental rinse of Example 1, and were instructed to use the rinse as follows:

a. Use one tablespoon of the dental rinse before each brushing. Rinse vigorously around the mouth for 30 seconds.

b. follow immediately with the usual brushing routine (toothbrush plus toothpaste), brushing thoroughly.

c. repeat steps (a) and (b) twice daily. All four test patients were examined prior to usage of the dental rinse ("Day 1" on chart below). Plaque area was monitored during the test period through the use of POH disclosing tablets in accordance with the standard Quigley & Hein Index. See G. A. Quigley and J. W. Hein, Comparative Cleaning Efficiency of Manual and Powered Brushing, J. Amer. Dent. Assn., Vol. 65:26 (1962).

Gingival inflammation was measured by the Loe & Silness Index (See, Journal of Periodontology, Vol. 36, pg. 178 (1965), Loe, Theilades, Jensen), employing the Ranfjord Index which uses 6 teeth, numbers 3, 9, 12, 19, 25 and 28. The results are summarized in Table 1.

TABLE 1

| Patient No. | Area of Plaque Day 1 | Area of Plaque Day 8 | % Reduction | Inflammation Day 1 | Inflammation Day 8 | % Reduction |
| --- | --- | --- | --- | --- | --- | --- |
| 1 | 2.38 | 1.60 | 33 | 1.67 | 1.21 | 28 |
| 2 | 2.75 | 1.77 | 36 | 1.58 | 1.25 | 21 |
| 3 | 1.44 | 1.00 | 31 | 0.95 | 0.63 | 34 |
| 4 | 2.29 | 1.43 | 38 | 1.04 | 0.54 | 48 |

The foregoing demonstrates that the dental rinse of this invention was an effective agent in significantly reducing both plaque and gingival inflammation over the test period, when used in a regular home dental care regimen.

EXAMPLE 3

The following formulations were prepared:

| Ingredient | Red | Green | Amber |
| --- | --- | --- | --- |
| sorbitol (70% aqueous soln.) | 15.50* | 15.50 | 15.50 |
| sodium salicylate | 0.20 | 0.20 | 0.20 |
| sodium borate | 0.20 | 0.20 | 0.20 |
| sodium benzoate | 2.00 | 2.00 | — |
| ethanol (95%) | 6.95 | 6.95 | 6.95 |
| flavor compound 4483T | 0.31 | — | .31 |
| peppermint oil | — | 0.15 | — |
| propylene glycol | — | 0.16 | — |
| polysorbate 20 | 0.84 | 0.84 | 0.84 |
| water | 73.20 | 73.75 | 75.95 |
| 1% FDC Red 40 | 0.80 | — | — |
| 2% FDC Green 3 | — | 0.25 | — |
| 1% FDC Brown mixture | — | — | 0.05 |

*Table values are given in weight percent on a composition basis.

A double blind study of the test formulations was conducted. Neither the dentist administering the test nor the patients who used the dental formulations set forth above knew any details about the composition of the rinse.

Five patients were randomly chosen to use the red, five patients to use the green and five randomly chosen patients to test the amber formulation. At the start of the test each patient was given an initial examination with plaque disclosure tablets. The plaque disclosure tablets contain a red dye which preferentially stains plaque but does not stain the clean enamel surfaces of the teeth. The percent surface areas of the inside and outside tooth surfaces covered with plaque were then estimated, tooth by tooth, by a dentist in accordance with the method of Quigley & Hein, mentioned above.

After the initial examination, five patients were given a bottle of the red formulation, five patients were given the green, and five patients the amber formulation. Each patient was instructed to rinse with the formulation they were given twice a day prior to brushing. The patients were each instructed to retain the rinse in their mouths for at least 30 seconds, moving it around in the mouth in order to insure that all of the tooth and gum surfaces were well soaked in the rinse. After completing the rinsing step, the patient was instructed to brush in accordance with his regular routine and using his own toothpaste. After seven days of use of the test formulation, the patients returned to the clinic for a re-examination of their dental surfaces in accordance with the same procedures employed at the start of the test. The results of the test are summarized in Table 2.

TABLE 2

| Patient | Initial Score (before test) | After 7 Days |
|---|---|---|
| Red Formula | | |
| #1 | 2.54* | 0.96 |
| #2 | 3.60 | 1.84 |
| #3 | 2.86 | 0.54 |
| #4 | 2.06 | 0.39 |
| #5 | 3.73 | 0.45 |
| Red Formula Averages | 2.96 | 0.84 |
| | (72% reduction) | |
| Green Formula | | |
| #1 | 3.13 | 0.67 |
| #2 | 2.82 | 0.71 |
| #3 | 2.54 | 0.73 |
| #4 | 3.14 | 0.00 |
| Green Formula Averages | 2.91 | 0.53 |
| | (82% reduction) | |
| Amber Formula | | |
| #1 | 1.19 | 1.04 |
| #2 | 3.24 | 2.24 |
| #3 | 2.70 | 3.20 |
| #4 | 3.37 | 2.63 |
| Amber Formula Averages | 2.63 | 2.28 |
| | (13% reduction) | |

*Plaque scores are averages of front and back readings of all teeth in each patient's mouth.

The foregoing demonstrates the ability of the dental rinse of this invention to loosen, dislodge and retard the buildup of plaque when the dental rinse is employed prior to brushing. It is noted that even in test formulations which did not include sodium benzoate, plaque was reduced by 13% over the test period, while the effect was unexpectedly enhanced to 72%-82% in the sodium benzoate containing formulations.

EXAMPLE 4

A dental rinse is formulated from the following components combined in the indicated weight percentages.

| Weight Percent | Component |
|---|---|
| 2.0 | Sodium Benzoate, NF |
| 0.2 | Sodium Salicylate, USP |
| 0.5 | Sodium Bicarbonate |
| 0.2 | Sodium Borate |
| 0.8 | FDC Red 40 (1% aq.) |
| 0.5 | Sodium Lauryl Sulfate, 94% |
| 0.8 | Polysorbate 20 |
| 0.3 | Flavor other than sodium saccharin |
| 7.0 | ethanol, 95% |
| 72.68 | water |
| 15.0 | Glycerin, USP |
| 0.02 | sodium saccharin |

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the invention as those of skill in the art will readily understand. Accordingly, such variations and modifications are considered to be within the purview and scope of the invention and the following claims.

What is claimed is:

1. A dental rinse composition for loosening and removing plaque present on dental surfaces consisting essentially of an aqueous or an aqueous and alcoholic carrier for the ingredients of said dental rinse composition, wherein the ingredients include: about 0.1% to about 10% by weight of said dental rinse composition of an oral surfactant, at least about 1% by weight of said composition of sodium benzoate effective to increase the amenability of said plaque to removal when said composition is applied to dental surfaces, said composition including an effective amount of a detergent builder, and having a pH of about 7.5 to about 10.

2. The dental rinse according to claim 1 wherein said surfactant is an anionic surfactant.

3. The dental rinse according to claim 1 wherein the oral surfactant comprises about 0.5% to about 2% by weight of said dental rinse composition, and wherein said dental rinse includes at least about 2% of sodium benzoate.

4. The dental rinse according to claim 1 wherein the surfactant is sodium lauryl sulfate.

5. The dental rinse according to claim 4 wherein the dental rinse composition includes at least about 2% by weight of sodium benzoate.

6. The dental rinse according to claim 1 wherein the carrier further includes in solution as said detergent builder an effective amount of a compound selected from the group consisting of orally compatible borate, carbonate or bicarbonate detergent builders or a mixture thereof, in addition to said sodium benzoate and oral surfactant.

7. The dental rinse according to claim 1 wherein the dental rinse includes about 0.1% to 1% by weight of sodium borate.

8. The dental rinse according to claim 6 wherein said sodium benzoate comprises at least about 2% by weight of said composition.

9. The dental rinse according to claim 1 wherein the composition comprises about 0.1% to about 1% by weight of sodium bicarbonate.

10. The dental rinse according to claim 4 wherein said composition comprises by weight at least 2% sodium benzoate and about 0.1% to about 1% of said detergent builder.

11. The dental rinse according to claim 1 wherein the dental rinse includes an effective amount of sodium salicylate.

12. The dental rinse according to claim 1 wherein said dental rinse includes about 0.1% to 3% of said sodium salicylate, and an alkali alkyl sulfate salt as said oral surfactant.

13. The dental rinse according to claim 6 wherein said composition includes an effective amount of sodium salicylate.

14. The dental rinse according to claim 1 wherein the composition further includes an effective amount of a wound healing agent.

15. The dental rinse according to claim 14 wherein said wound healing agent is allantoin.

16. The dental rinse according to claim 1 wherein said composition comprises by weight about 2% sodium benzoate and about 0.1% to 3% sodium salicylate effective to aid in solubilizing plaque on said dental surfaces.

17. The dental rinse according to claim 1 wherein said carrier comprises about 65% to about 95% water and about 5% to about 35% alcohol, said ingredients of said composition are dissolved therein, and said oral surfactant is sodium lauryl sulfate.

18. The dental rinse according to claim 1 wherein the composition includes a solvent of alcohol and water for the ingredients of said dental rinse, about 0.5% to about 2% of an oral surfactant, about 0.1% to 1% of sodium borate, about 0.3% to about 0.8% sodium bicarbonate, and at least about 2% sodium benzoate.

19. The dental rinse according to claim 1 wherein said composition further includes up to about 20% by weight of glycerine, allantoin, and about 0.1% to about 3% by weight of sodium salicylate.

20. The dental rinse according to claim 1 wherein said composition comprises at least about 2% sodium benzoate, about 0.1% to 1% sodium bicarbonate, about 0.1% to 1% sodium borate, up to about 20% by weight of glycerine, about 0.1% to about 3% sodium salicylate, and wherein said carrier comprises about 70% to 95% of said composition and said carrier is comprised of about 65% to about 95% water and about 5% to about 35% ethanol, said composition further including allantoin, xanthan gum, and minor effective amounts of flavorant.

21. The dental rinse according to claim 20 wherein said surfactant is sodium lauryl sulfate.

22. The dental rinse according to claim 1 wherein said composition includes minor effective amounts of flavorant and colorant and the pH of the composition is about 7.5.

23. The dental rinse according to claim 1 including at least about 2% of sodium benzoate and as said oral surfactant an alkali alkyl sulfate salt wherein said alkyl portion of said surfactant is substituted or unsubstituted.

24. The dental rinse according to claim 23 wherein said alkyl portion of said sulfate salt has about 9 to about 15 carbon atoms.

25. The dental rinse according to claim 1 wherein said oral surfactant is sulfosuccinate or sarcosinate surfactant.

26. The dental rinse according to claim 1 wherein said surfactant is a nonionic surfactant.

27. The dental rinse according to claim 1 wherein said oral surfactant is sodium lauryl sulfate which comprises about 0.1% to about 1.5% of said composition.

28. A composition suitable for application to dental surfaces to render the plaque thereon amenable to removal by brushing consisting essentially of an aqueous or an aqueous and alcoholic carrier, at least about 1% sodium benzoate, at least about 0.1% to about 1% of a detergent builder, about 0.1% to about 1% by weight of an oral surfactant, and minor effective amounts of colorant and flavorant.

* * * * *